(12) United States Patent
Jiang et al.

(10) Patent No.: US 9,228,235 B2
(45) Date of Patent: Jan. 5, 2016

(54) METHOD AND KIT FOR THE CLASSIFICATION AND PROGNOSIS OF CHRONIC WOUNDS

(75) Inventors: Wen Guo Jiang, Cardiff (GB); Keith Gordon Harding, Cardiff (GB)

(73) Assignee: University College Cardiff Consultants Limited, Cardiff (GB)

( * ) Notice: Subject to any disclaimer, the term of this patent is extended or adjusted under 35 U.S.C. 154(b) by 178 days.

(21) Appl. No.: 13/326,153

(22) Filed: Dec. 14, 2011

(65) Prior Publication Data

US 2012/0315637 A1 Dec. 13, 2012

(30) Foreign Application Priority Data

Dec. 14, 2010 (GB) .................................. 1021182.9

(51) Int. Cl.
*C12Q 1/68* (2006.01)
*C12P 19/34* (2006.01)
(52) U.S. Cl.
CPC ........ *C12Q 1/6883* (2013.01); *C12Q 2600/112* (2013.01); *C12Q 2600/158* (2013.01)
(58) Field of Classification Search
None
See application file for complete search history.

(56) References Cited

U.S. PATENT DOCUMENTS

| | | | |
|---|---|---|---|
| 2005/0170445 A1 | 8/2005 | Reichert et al. | |
| 2006/0275770 A1 | 12/2006 | Bednarik | |

FOREIGN PATENT DOCUMENTS

| | | | |
|---|---|---|---|
| CN | 101671729 A | * | 3/2010 |
| WO | 9634117 | | 10/1996 |
| WO | 0162276 A1 | | 8/2001 |
| WO | 03075949 A1 | | 9/2003 |
| WO | 2004005312 A1 | | 1/2004 |
| WO | 2004050894 | | 6/2004 |
| WO | 2004070002 A2 | | 8/2004 |
| WO | 2005028681 | | 3/2005 |
| WO | 2006053162 A1 | | 5/2006 |
| WO | 2006108225 | | 10/2006 |
| WO | 2007130423 | | 11/2007 |
| WO | 2009076229 | | 6/2009 |
| WO | 2010065995 | | 6/2010 |
| WO | 2010085606 | | 7/2010 |
| WO | 2011033249 A1 | | 3/2011 |

OTHER PUBLICATIONS

GeneCards® CAR1; http://www.genecards.org/index.php?path=/Search/keyword/car1, accessed on Jun. 10, 2013.*
Vandesompele et al. Accurate normalization of real-time quantitative RT-PCR data by geometric averaging of multiple internal control genes. Genome Biology 2002;3(7):0034.1.0034.11.*
Affymetrix. Human Genome U133A Array Annotation data, 2009.*
Affymetrix. Human Genome U133B Array Annotation data, 2009.*
Machine translation of CN 101671729 A; obtained Feb. 4, 2014; pp. 1-7.*
Burchert, et al., "CD82 (KAI1), a member of the tetraspan family, is expressed on early haemopoietic progenitor cells and up-regulated in distinct human leukaemias", Bri. J Haematology, 107:494-504 (1999).
Cooper, et al., "Wound healing and inflammation genes revealed by array analysis of macrophageless\ PU.I null mice" , Genome Biol., 6:R5.1-R5.17 (2004).
Almeida, et al.; "Randomized, double-blind study of stibogluconate plus human granulocyte macrophage colony-stimulating factor versus stibogluconate alone in the treatment of cutaneous Leishmaniasis"; The Journal of Infectious Diseases, vol. 180, No. 5, pp. 1735-1737 (Oct. 8, 1999).
Derrick, et al.; "Comparative analysis of global gene expression profiles between diabetic rat wounds treated with vacuum-assisted closure therapy, moist wound healing or gauze under suction"; International Wound Journal, vol. 5, No. 5, pp. 615-624, (Dec. 2008).
Hardiman, et al.; "Microarray platforms—comparisons and contrasts"; Pharmacogenomics (2004), vol. 5, No. 5, pp. 487-502.
Martinez, et al.; "Treatment of Cutaneous Leishmaniasis with Allopurinol and Stibogluconate"; Clinical Infectious Diseases, vol. 24, No. 2, pp. 165-169 (Feb. 1, 1997).
Moseley et al.; "Extracellular matrix metabolites as potential biomarkers of disease activity in wound fluid: lessons learned from other inflammatory diseases?"; British Journal of Dermatology vol. 150, No. 3, pp. 401-413 (Mar. 1, 2004).
Solomon et al.; "Treatment of cutaneous leishmaniasis with intralesional sodium stibogluconate"; Journal of the European Academy of Dermatology and Venereology, vol. 23, No. 10, pp. 1189-1192, (Oct. 1, 2009).
Wang, et al.; "Transforming Growth Factor β (TGF-β)-Smad Target Gene Protein Tyrosine Phosphatase Receptor Type Kappa is Required for TGF-β Function"; Molecular and Cellular Biology, Jun. 2005, vol. 25, No. 11, pp. 4703-4715.
Xu, et al.; "Receptor-type Protein-tyrosine Phosphatase-κ Regulates Epidermal Growth Factor Receptor Function"; Journal of Biological Chemistry, vol. 280, No. 52, pp. 42694-42700 (Jan. 1, 2005).
International Search Report and Written Opinion for International Application No. PCT/GB2010/001696 dated Nov. 5, 2010.
International Search Report and Written Opinion for International Application No. PCT/GB2010/050362 dated May 24, 2012.
Search Report for British Application No. GB1103898.1 dated Jul. 7, 2011.

* cited by examiner

*Primary Examiner* — Young J Kim
(74) *Attorney, Agent, or Firm* — Kling & Schickli, PLLC

(57) ABSTRACT

A method and kit are provided for identifying non-healing or healing chronic mammalian wound tissue or for determining the prognosis of chronic mammalian wound tissue based upon the identification of at least one key set of molecular markers or genes whose expression pattern is indicative of a given wound type and so representative of a given prognosis.

9 Claims, 3 Drawing Sheets

```
                          SEQUENCE LISTING

<160> NUMBER OF SEQ ID NOS: 50

<210> SEQ ID NO 1
<211> LENGTH: 20
<212> TYPE: DNA
<213> ORGANISM: Homo sapiens

<400> SEQUENCE: 1
attgagcaag agcagaaact                                                  20

<210> SEQ ID NO 2
<211> LENGTH: 38
<212> TYPE: DNA
<213> ORGANISM: Homo sapiens

<400> SEQUENCE: 2
actgaacctg accgtacatt ctggtgcttc aaatctct                              38

<210> SEQ ID NO 3
<211> LENGTH: 20
<212> TYPE: DNA
<213> ORGANISM: Homo sapiens

<400> SEQUENCE: 3
agatgaagaa tggcaaagaa                                                  20

<210> SEQ ID NO 4
<211> LENGTH: 37
<212> TYPE: DNA
<213> ORGANISM: Homo sapiens

<400> SEQUENCE: 4
actgaacctg accgtacaat ctgctgttca gatcgtt                               37

<210> SEQ ID NO 5
<211> LENGTH: 20
<212> TYPE: DNA
<213> ORGANISM: Homo sapiens

<400> SEQUENCE: 5
catctcaccc tggagatacc                                                  20

<210> SEQ ID NO 6
<211> LENGTH: 36
<212> TYPE: DNA
<213> ORGANISM: Homo sapiens

<400> SEQUENCE: 6
actgaacctg accgtacaca tcgatacagc ctctgc                                36
```

-continued

```
<210> SEQ ID NO 7
<211> LENGTH: 20
<212> TYPE: DNA
<213> ORGANISM: Homo sapiens

<400> SEQUENCE: 7
gctgctgcac attataacac                                               20

<210> SEQ ID NO 8
<211> LENGTH: 38
<212> TYPE: DNA
<213> ORGANISM: Homo sapiens

<400> SEQUENCE: 8
actgaacctg accgtacaaa ctccttcccc acatctat                           38

<210> SEQ ID NO 9
<211> LENGTH: 20
<212> TYPE: DNA
<213> ORGANISM: Homo sapiens

<400> SEQUENCE: 9
agggattttc tcagtccttc                                               20

<210> SEQ ID NO 10
<211> LENGTH: 38
<212> TYPE: DNA
<213> ORGANISM: Homo sapiens

<400> SEQUENCE: 10
actgaacctg accgtacaca tgccctcatc taatgtct                           38

<210> SEQ ID NO 11
<211> LENGTH: 18
<212> TYPE: DNA
<213> ORGANISM: Homo sapiens

<400> SEQUENCE: 11
catccaccca gtgccaac                                                 18

<210> SEQ ID NO 12
<211> LENGTH: 36
<212> TYPE: DNA
<213> ORGANISM: Homo sapiens

<400> SEQUENCE: 12 actgaac ctgaccgtac accacacagt cagccacag                             36

<210> SEQ ID NO 13
<211> LENGTH: 20
<212> TYPE: DNA
<213> ORGANISM: Homo sapiens

<400> SEQUENCE: 13
aaatgttgtc acaccaacaa                                               20

<210> SEQ ID NO 14
<211> LENGTH: 38
<212> TYPE: DNA
<213> ORGANISM: Homo sapiens

<400> SEQUENCE: 14
actgaacctg accgtacaag ctgttgacat cagagaca                           38
```

<210> SEQ ID NO 15
<211> LENGTH: 20
<212> TYPE: DNA
<213> ORGANISM: Homo sapiens

<400> SEQUENCE: 15
agatgactga caggttcagc                                                    20

<210> SEQ ID NO 16
<211> LENGTH: 38
<212> TYPE: DNA
<213> ORGANISM: Homo sapiens

<400> SEQUENCE: 16
actgaacctg accgtacaga atcgatctca ctttggag                                38

<210> SEQ ID NO 17
<211> LENGTH: 20
<212> TYPE: DNA
<213> ORGANISM: Homo sapiens

<400> SEQUENCE: 17
cagctgacta cccaactctg                                                    20

<210> SEQ ID NO 18
<211> LENGTH: 36
<212> TYPE: DNA
<213> ORGANISM: Homo sapiens

<400> SEQUENCE: 18
actgaacctg accgtacaat ctgcaccagt gaaagg                                  36

<210> SEQ ID NO 19
<211> LENGTH: 21
<212> TYPE: DNA
<213> ORGANISM: Homo sapiens

<400> SEQUENCE: 19
tcaaattcat atgtctcagc a                                                  21

<210> SEQ ID NO 20
<211> LENGTH: 36
<212> TYPE: DNA
<213> ORGANISM: Homo sapiens

<400> SEQUENCE: 20
actgaacctg accgtacagt tgcccatgtc ctcata                                  36

<210> SEQ ID NO 21
<211> LENGTH: 18
<212> TYPE: DNA
<213> ORGANISM: Homo sapiens

<400> SEQUENCE: 21
ttcctggacc acaacatc                                                      18

<210> SEQ ID NO 22
<211> LENGTH: 38
<212> TYPE: DNA
<213> ORGANISM: Homo sapiens

<400> SEQUENCE: 22
actgaacctg accgtacaca ccgagtcgta cactttgc                                38

```
<210> SEQ ID NO 23
<211> LENGTH: 20
<212> TYPE: DNA
<213> ORGANISM: Homo sapiens

<400> SEQUENCE: 23
cttgattggc agtatggagt                                                   20

<210> SEQ ID NO 24
<211> LENGTH: 37
<212> TYPE: DNA
<213> ORGANISM: Homo sapiens

<400> SEQUENCE: 24
actgaacctg accgtacagt ctaccgcctt gagaaag                                37

<210> SEQ ID NO 25
<211> LENGTH: 20
<212> TYPE: DNA
<213> ORGANISM: Homo sapiens

<400> SEQUENCE: 25
tatggctgta cctccattgt                                                   20

<210> SEQ ID NO 26
<211> LENGTH: 38
<212> TYPE: DNA
<213> ORGANISM: Homo sapiens

<400> SEQUENCE: 26
actgaacctg accgtacaat atcgtagcat cccttcct                               38

<210> SEQ ID NO 27
<211> LENGTH: 18
<212> TYPE: DNA
<213> ORGANISM: Homo sapiens

<400> SEQUENCE: 27
gtgaagccct tgaccagt                                                     18

<210> SEQ ID NO 28
<211> LENGTH: 38
<212> TYPE: DNA
<213> ORGANISM: Homo sapiens

<400> SEQUENCE: 28
actgaacctg accgtacatt ggtatagtcc tcggtttg                               38

<210> SEQ ID NO 29
<211> LENGTH: 19
<212> TYPE: DNA
<213> ORGANISM: Homo sapiens

<400> SEQUENCE: 29
ggtgctactc ctctgcatt                                                    19

<210> SEQ ID NO 30
<211> LENGTH: 37
<212> TYPE: DNA
<213> ORGANISM: Homo sapiens

<400> SEQUENCE: 30
```

```
actgaacctg accgtacaag aaaggatcct cctcctc                              37

<210> SEQ ID NO 31
<211> LENGTH: 18
<212> TYPE: DNA
<213> ORGANISM: Homo sapiens

<400> SEQUENCE: 31
agtcctcctg gctgacaa                                                   18

<210> SEQ ID NO 32
<211> LENGTH: 36
<212> TYPE: DNA
<213> ORGANISM: Homo sapiens

<400> SEQUENCE: 32
actgaacctg accgtacaca cagcctcatc caacac                               36

<210> SEQ ID NO 33
<211> LENGTH: 20
<212> TYPE: DNA
<213> ORGANISM: Homo sapiens

<400> SEQUENCE: 33
gagctggatg agaacaacac                                                 20

<210> SEQ ID NO 34
<211> LENGTH: 38
<212> TYPE: DNA
<213> ORGANISM: Homo sapiens

<400> SEQUENCE: 34
actgaacctg accgtacaaa agaagtggca ggaagagt                             38

<210> SEQ ID NO 35
<211> LENGTH: 20
<212> TYPE: DNA
<213> ORGANISM: Homo sapiens

<400> SEQUENCE: 35
cctacacagc ggtcagatag                                                 20

<210> SEQ ID NO 36
<211> LENGTH: 38
<212> TYPE: DNA
<213> ORGANISM: Homo sapiens

<400> SEQUENCE: 36
actgaacctg accgtacaag cagaagtttc tccctctt                             38

<210> SEQ ID NO 37
<211> LENGTH: 20
<212> TYPE: DNA
<213> ORGANISM: Homo sapiens

<400> SEQUENCE: 37
aacttcccca acttccttag                                                 20

<210> SEQ ID NO 38
<211> LENGTH: 38
<212> TYPE: DNA
<213> ORGANISM: Homo sapiens

<400> SEQUENCE: 38
```

```
actgaacctg accgtacaag caaggacaga aactcaga                              38

<210> SEQ ID NO 39
<211> LENGTH: 18
<212> TYPE: DNA
<213> ORGANISM: Homo sapiens

<400> SEQUENCE: 39
atgccaggag acgacctc                                                   18

<210> SEQ ID NO 40
<211> LENGTH: 38
<212> TYPE: DNA
<213> ORGANISM: Homo sapiens

<400> SEQUENCE: 40
actgaacctg accgtacaga tcttacgctt cccttacc                             38

<210> SEQ ID NO 41
<211> LENGTH: 17
<212> TYPE: DNA
<213> ORGANISM: Homo sapiens

<400> SEQUENCE: 41
gtctcgttca agctggg                                                    17

<210> SEQ ID NO 42
<211> LENGTH: 36
<212> TYPE: DNA
<213> ORGANISM: Homo sapiens

<400> SEQUENCE: 42
actgaacctg accgtacagg ttgccgtgtc ctcctc                               36

<210> SEQ ID NO 43
<211> LENGTH: 20
<212> TYPE: DNA
<213> ORGANISM: Homo sapiens

<400> SEQUENCE: 43
agtgactggg gatagtgaag                                                 20

<210> SEQ ID NO 44
<211> LENGTH: 38
<212> TYPE: DNA
<213> ORGANISM: Homo sapiens

<400> SEQUENCE: 44
actgaacctg accgtacaca gagcacaact gttccttt                             38

<210> SEQ ID NO 45
<211> LENGTH: 40
<212> TYPE: DNA
<213> ORGANISM: Homo sapiens

<400> SEQUENCE: 45
cattcgagac tacaacagca ctgtactttg ctttcctgct                           40

<210> SEQ ID NO 46
<211> LENGTH: 20
<212> TYPE: DNA
<213> ORGANISM: Homo sapiens
```

```
<400> SEQUENCE: 46
ctgtagtctt cggaatggac                                               20

<210> SEQ ID NO 47
<211> LENGTH: 20
<212> TYPE: DNA
<213> ORGANISM: Homo sapiens

<400> SEQUENCE: 47
atggatctga agaaattgga                                               20

<210> SEQ ID NO 48
<211> LENGTH: 38
<212> TYPE: DNA
<213> ORGANISM: Homo sapiens

<400> SEQUENCE: 48
actgaacctg accgtacaag acaattttg ccactcat                            38

<210> SEQ ID NO 49
<211> LENGTH: 20
<212> TYPE: DNA
<213> ORGANISM: Homo sapiens

<400> SEQUENCE: 49
ggggactatg aggagatgat                                               20

<210> SEQ ID NO 50
<211> LENGTH: 38
<212> TYPE: DNA
<213> ORGANISM: Homo sapiens

<400> SEQUENCE: 50
actgaacctg accgtacagt ggaggtcttg atgtgaat                           38
```

METHOD AND KIT FOR THE CLASSIFICATION AND PROGNOSIS OF CHRONIC WOUNDS

CROSS REFERENCE TO RELATED APPLICATIONS

This application claims benefit of and priority to foreign application GB1021182.9, filed in the Intellectual Property Office on Dec. 14, 2010, which is incorporated herein by reference in its entirety.

REFERENCE TO SEQUENCE LISTING

The Sequence Listing submitted Dec. 14, 2011, as a text file named "UCC_0029AP_Sequence_Listing.txt," created on Dec. 9, 2011, and having a size of 7,567 bytes, is hereby incorporated by reference.

FIELD OF THE INVENTION

The present invention relates to a method and kit, including parts thereof, for the classification and prognosis of chronic mammalian and, in particular, human wounds. More specifically, the method involves identifying one or more gene expression patterns that enables one to distinguish between 'abnormal or non-healing' chronic wounds or healing chronic wounds. Advantageously, the said gene expression pattern(s) allows informed decision making in the selection of treatment and the prediction of outcome following use of a given therapy. Further the invention identifies new targets for use in wound therapy.

BACKGROUND OF THE INVENTION

In one form or another, non-healing or chronic and poorly healing wounds constitute a major burden on the UK health system. Moreover, in certain member countries of the EU health expenses relating to wound healing are already approaching the third most expensive drain on health care funding.

Chronic foot ulcers are a major complication of diabetes, accounting for up to 25% of all hospital admissions involving diabetes, and at a cost to the UK National Health Service of £250M annually. Chronic foot ulcers cause substantial morbidity, impair the quality of life, and are the major cause of lower limb amputation. Despite careful attention to foot care, as many as 25% of diabetics develop foot ulcers in their lifetimes. The causes of lower limb ulceration are the same in diabetics as in non-diabetics, namely neuropathy, ischaemia and trauma. However, this "pathogenic triad" predisposes wounds to infection, which can also contribute to the non-healing nature of the wounds.

Current treatment involves removing pressure from the area, debridement, wound dressing and management of infection: surgical resection and vascular reconstruction may be required in more advanced disease, which ultimately may necessitate amputation.

In addition to lower limb ulcers in diabetics, another major resource health cost is created by pressure wounds or ulcers that result, for example, from failure to provide routine nursing or medical care. In the UK 412,000 people are affected annually by this sort of wound at a cost of £1.4-2.1 billion.

The healing of a wound is controlled by complex biological processes that involve a diverse number of cell types; complex interactions between cells and tissues; the activation of the immune system and the activation of the angiogenic process.

A typical healing process can be divided into 5 distinct, but closely related, stages: clotting stage, acute inflammation stage, matrix deposition stage, capillary formation stage and re-epithelialisation stage. A diverse number of factors control each of these stages. Deficiencies in any aspect of the process can result in defective wound healing. Thus, a 'normal' healing process can be defective as a result of either intrinsic or external factors, which manifest as 'abnormal non-healing' or 'chronic' wounds. It is these 'non-healing' or chronic wounds that present the greatest challenge to the quality of a patient's life and mounting expenses to the healthcare system.

Although some common clinical/pathological factors may assist in pre judging if a wound is 'healing' or 'non-healing', or if an acute wound becomes chronic, there is no specific laboratory test(s) to distinguish wound type. Additionally, there is no clear way to define how to predict the healing process and a patient's likely response to treatment in wound care.

SUMMARY OF THE INVENTION

A method for determining the prognosis of a given wound which is relatively straightforward to perform, efficient to undertake and provides an accurate indication of the likely outcome, before or during treatment, of a wound has been developed. The method uses a small but highly representative sample of markers which distinguishes between acute wounds, chronic wounds and non-healing wounds and is therefore particularly relevant in the selection of treatment for a given wound and particularly accurate in determining the likely outcome, following treatment, of a given wound.

A plurality of molecular markers have been identified that have relevance in determining the prognosis of a given wound. Collectively these markers constitute at least one molecular signature and the expression of these markers in wound tissue from a patient constitutes a gene expression pattern that is indicative of a given wound type and prognosis. In addition to this, the said molecular signature has been analyzed in order to identify which markers are the best indicators of wound type and prognosis. In other words, the molecular signature includes those biomarkers that contribute most to the predictive ability of the molecular signature. This subset of markers is known, collectively, as the refined molecular signature and the expression of these markers constitutes a refined gene expression pattern.

Additionally, this refined molecular signature has been examined to determine if it contains a sub-set of genes that could be used to provide a further acceptable indication of wound healing. This subset of markers is known, collectively, as the super refined molecular signature and the expression of these markers constitutes a super refined gene expression pattern.

The elucidation of the molecular signatures described herein has involved the systematic and careful examination of, in the first instance, 34 samples of wound tissue and 110 genetic molecular markers and, in the second instance where validation studies have been performed, 71 samples of wound tissue and the use of the markers described herein.

Very few genes need to be examined in order to provide an accurate classification and prognosis for a given sample of wound tissue. This number has been further reduced by identifying those molecular markers that contribute most to the predictive ability of the molecular signature. For example, only 25 or, more ideally, 14, or more ideally still only 4, genes need to be examined. This means that the methods have immediate application and can be performed quickly and routinely in a clinical context. In fact, the methods can form part of the standard treatment regime of wound care so that the relevant clinician can, at an early stage, determine the classification and outcome of a particular wound and match the treatment accordingly. For example, in the case of an individual who presents with a signature indicative of an 'abnormal or non-healing' chronic wound one would prescribe a different form of treatment than the treatment prescribed to a patient presenting with a healing chronic wound. The method not only serves to ensure that individuals receive treatment tailored to their wound status, but it can improve the quality of a patient's life during treatment, by ensuring that aggressive therapy is only prescribed in those cases where it is necessary.

DETAILED DESCRIPTION OF THE INVENTION

I. Methods of Identifying Non-Healing Wounds

Figure 1:
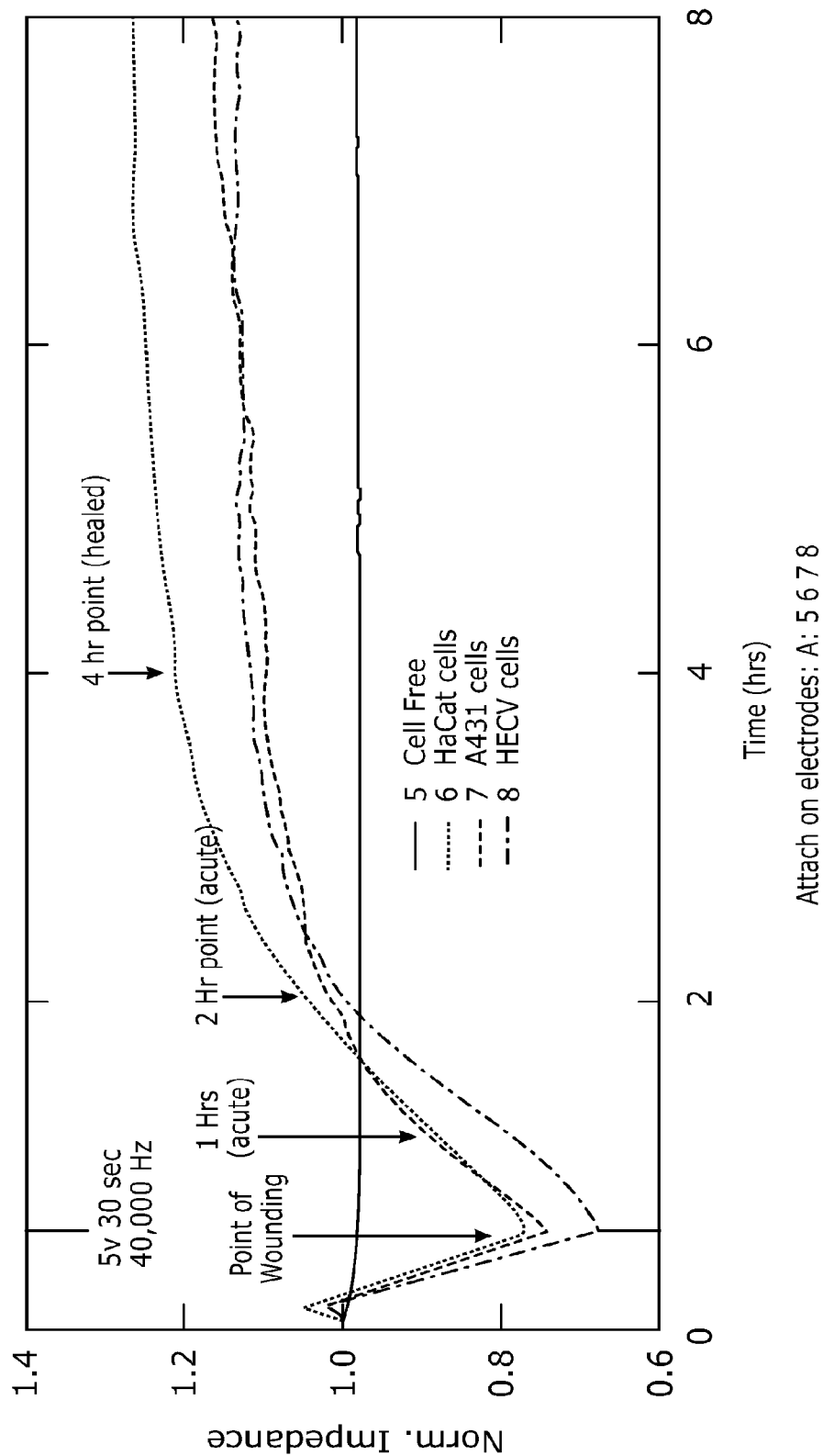
FIG. 1 shows monitoring of the healing process by electric cell sensing (ECIS). A monolayer of cells in the ECIS chambers were wounded at 5 v 30 sec (indicated). The change of electric impedance was monitored before and after wounding. Three hours after wounding, the migration/healing reached its stable phase.

Several molecular marker signatures have been identified. The molecular marker signatures can be used to identify non-healing and healing wounds. A fourteen (14) gene refined gene signature was determined (Table 3). This 14 molecular marker signature can be further refined into a 4 gene super refined gene signature (Table 4). Those skilled in the art will appreciate that both the 14 gene refined gene signature and the 4 gene super refined gene signature can be used simultaneously or successively. When the 14 gene refined gene signature is used it contains within it the super refined gene signature and therefore both signatures are in fact used simultaneously. The 4 gene super refined signature can be used in isolation of the 14 gene refined gene signature or followed by the 14 gene refined gene signature. When it is followed by the 14 gene refined gene signature, only the 10 genes not examined in the 4 gene super refined gene signature need to be examined.

TABLE 3

The 14 gene refined signature list

ARP2
CREBL1
VEGF-C
Psoriasin
IL22R
TEM4
IL8RB
IL17BR

TABLE 3-continued

The 14 gene refined signature list

Claudin-5
KAI1
PTPRK
CAR1
Endomucin-2
TEM7R

TABLE 4

The 4 gene super refined signature list

ARP2
CREBL1
PTPRK
TEM7R

4 Gene Super Refined Gene Signature Markers

The 4 gene super refined gene signature can be used to provide the method for identifying abnormal or non-healing chronic mammalian wound tissue. The method can include determining the levels of expression of genes encoding the following molecular markers: ARP2, CREBL1, PTPRK, and TEM7R. an increased level of expression of PTPRK, TEM7R, and ARP2 indicates that the wound tissue is an abnormal or non-healing chronic wound. Normal or decreased levels of CREBL1 indicate the wound is a non-healing chronic wound.

The methods can involve determining levels of all 4 of the 4 gene super refined gene signature or can involve only determining the levels of PTPRK, TEM7R, and ARP2. CREBL1 expression levels can be determined with the other three molecular markers or can be determined separate. In some instances, it is not necessary to determine the levels of CREBL1 because an increased level of expression of PTPRK, TEM7R, and ARP2 indicates that the wound tissue is an abnormal or non-healing chronic wound without even testing for CREBL1 levels.

14 Gene Signature Markers

Methods for identifying abnormal or non-healing chronic mammalian wound tissue are provided. The methods can include determining the levels of expression of at least the molecular markers Psoriasin, Claudin-5, IL8RB, IL22R, PTPRK, TEM4, TEM7R, VEGF-C, ARP2 and CAR1 from a sample of wound tissue. An increased level of expression compared to a control indicates the wound is an abnormal or non-healing chronic wound.

In some embodiments, expression levels of all 14 gene refined gene signature markers (ARP2, CREBL1, VEGF-C, Psoriasin, IL22R, TEM4, IL8RB, IL17BR, Claudin-5, KAI1, PTPRK, CAR1, Endomucin-2, and TEM7R) are determined. In some cases expression levels of Psoriasin, Claudin-5, IL8RB, IL22R, PTPRK, TEM4, TEM7R, VEGF-C, ARP2 and CAR1 will have already been determined therefore expression levels of only CREBL1, IL17BR, KAI1 and 2 Endomucin-2 are left to be determined. A decreased or normal expression level of CREBL1, IL17BR, KAI1 and Endomucin-2 can be indicative of abnormal or non-healing chronic wounds.

25 Gene Signature Markers

Table 1 provides a list of 25 molecular markers that can be used to identify acute and chronic wounds. These markers can further be used to identify healing and non-healing wounds. In some instances the wounds are chronic wounds. Table 2 shows the primers used to quantify the expression of the genes shown in Table 1. Certain combinations of the markers listed in Table 1 can be used.

One or more of the 25 gene signature markers can be used to determine if a wound is healing or non-healing.

TABLE 1

The 25 gene signature list

| Molecule name | Change in human wounds |
|---|---|
| ARP2 | Decreased in chronic and increased in acute wounds |
| VEGF-D | Decreased in chronic and increased in acute wounds |
| IL17C | Decreased in chronic and increased in acute wounds |
| VEGF-C | Decreased in chronic wounds |
| beta-Catenin | Decreased in chronic wounds |
| RON | Decreased in chronic and increased in acute wounds |
| Endomucin-2 | Decreased in chronic wounds |
| IL22R | Increased in both acute and chronic wounds |

TABLE 1-continued

The 25 gene signature list

| Molecule name | Change in human wounds |
|---|---|
| WAVE2 | High in acute |
| IL8RB | Decreased in chronic and increased in acute wounds |
| Claudin-5 | Decreased in chronic and increased in acute wounds |
| TEM7R | Increased in both acute and chronic wounds |
| PTPRK | Increased in both acute and chronic wounds |
| BMP15 | Decreased in chronic wounds |
| PEDF | Decreased in human wounds |
| RhoGDI-G | Decreased in human wounds |
| N-WASP | Decreased in chronic and increased in acute wounds |
| AMFR | High in acute |
| Psoriasin | Increased in both acute and chronic wounds |
| Par4 | High in acute |
| TEM4 | High in acute |
| IL17BR | Decreased in chronic and increased in acute wounds |
| KAI1 | Increased in both acute and chronic wounds |
| CAR1 | Decreased in chronic and increased in acute wounds |
| CREBL1 | Decreased in chronic and increased in acute wounds |

TABLE 2

Primers for the 25 gene signature list

| MOLECULE NAME | PRIMER PAIR (5'-'3) |
|---|---|
| ARP2 | attgagcaagagcagaaact, (SEQ ID NO: 1) and actgaacctgaccgtacattaggtgcttcaaatctct (SEQ ID NO: 2) |
| VEGF-D | agatgaagaatggcaaagaa, (SEQ ID NO: 3) and actgaacctgaccgtacaatctgctgttcagatcgtt (SEQ ID NO: 4) |
| IL17C | catctcaccctggagatacc, (SEQ ID NO: 5) and actgaacctgaccgtacacatcgatacagcctctgc (SEQ ID NO: 6) |
| VEGF-C | gctgctgcacattataacac, (SEQ ID NO: 7) and actgaacctgaccgtacaaactccttccccacatctat (SEQ ID NO: 8) |
| β-Catenin | agggattttctcagtccttc, (SEQ ID NO: 9) and actgaacctgaccgtacacatgccctcatctaatgtct (SEQ ID NO: 10) |
| RON | catccacccagtgccaac, (SEQ ID NO: 11) and actgaacctgaccgtacaccacacagtcagccacag (SEQ ID NO: 12) |
| Endomucin-2 | aaatgttgtcacaccaacaa, (SEQ ID NO: 13) and actgaacctgaccgtacaagctgttgacatcagagaca (SEQ ID NO: 14) |
| IL22R | agatgactgacaggttcagc, (SEQ ID NO: 15) and actgaacctgaccgtacagaatcgatctcacttggag (SEQ ID NO: 16) |

TABLE 2-continued

Primers for the 25 gene signature list

| MOLECULE NAME | PRIMER PAIR (5'-'3) |
|---|---|
| WAVE2 | cagctgactacccaactctg, (SEQ ID NO: 17) and actgaacctgaccgtacaatctgcaccagtgaaagg (SEQ ID NO: 18) |
| IL8RB | tcaaattcatatgtctcagca, (SEQ ID NO: 19) and actgaacctgaccgtacagttgcccatgtcctcata (SEQ ID NO: 20) |
| Claudin-5 | ttcctggaccacaacatc, (SEQ ID NO: 21) and actgaacctgaccgtacacaccgagtcgtacactttgc (SEQ ID NO: 22) |
| TEM7R | cttgattggcagtatggagt, (SEQ ID NO: 23) and actgaacctgaccgtacagtctaccgccttgagaaag (SEQ ID NO: 24) |
| PTPRK | tatggctgtacctccattgt, (SEQ ID NO: 25) and actgaacctgaccgtacaatatcgtagcatcccttcct (SEQ ID NO: 26) |
| BMP15 | gtgaagcccttgaccagt, (SEQ ID NO: 27) and actgaacctgaccgtacattggtatagtcctcggtttg (SEQ ID NO: 28) |
| PEDF | ggtgctactcctctgcatt, (SEQ ID NO: 29) and actgaacctgaccgtacaagaaaggatcctcctcctc (SEQ ID NO: 30) |
| RHOGDI-G | agtcctcctggctgacaa, (SEQ ID NO: 31) and actgaacctgaccgtacacacagcctcatccaacac (SEQ ID NO: 32) |
| N-WASP | gagctggatgagaacaacac, (SEQ ID NO: 33) and actgaacctgaccgtacaaaagaagtggcaggaagagt (SEQ ID NO: 34) |
| AMFR | cctacacagcggtcagatag, (SEQ ID NO: 35) and actgaacctgaccgtacaagcagaagtttctccctctt (SEQ ID NO: 36) |
| Psoriasin | aacttccccaacttccttag, (SEQ ID NO: 37) and actgaacctgaccgtacaagcaaggacagaaactcaga (SEQ ID NO: 38) |
| PAR4 | atgccaggagacgacctc, (SEQ ID NO: 39) and actgaacctgaccgtacagatcttacgcttcccttacc (SEQ ID NO: 40) |
| TEM4 | gtctcgttcaagctggg, (SEQ ID NO: 41) and |

TABLE 2-continued

Primers for the 25 gene signature list

| MOLECULE NAME | PRIMER PAIR (5'-'3) |
|---|---|
| | actgaacctgaccgtacaggttgccgtgtcctcctc (SEQ ID NO: 42) |
| IL17BR | agtgactggggatagtgaag, (SEQ ID NO: 43) and actgaacctgaccgtacacagagcacaactgttcctt (SEQ ID NO: 44) |
| KAI1 | cattcgagactacaacagca ctgtactttgctttcctgct, (SEQ ID NO: 45) and ctgtagtcttcggaatggac (SEQ ID NO: 46) |
| CAR1 | atggatctgaagaaattgga, (SEQ ID NO: 47) and actgaacctgaccgtacaagacaattttttgccactcat (SEQ ID NO: 48) |
| CREBL1 | ggggactatgaggagatgat, (SEQ ID NO: 49) and actgaacctgaccgtacagtggaggtcttgatgtgaat (SEQ ID NO: 50)) |

II. Methods of Identifying Healing Wounds

Also provided are methods for identifying healing chronic mammalian wound tissue. The methods can include determining the levels of expression of the following molecular markers: ARP2, CREBL1, VEGF-C, Psoriasin, IL22R, TEM4, IL8RB, IL17BR, Claudin-5, KAI1, PTPRK, CAR1, Endomucin-2, and TEM7R. The methods can include determining expression levels of all 14 markers or determining expression levels of different subsets of these markers.

In one embodiment, only expression levels of CREBL1, IL17BR, KAI1 and Endomuscin-2 are determined. A decreased level of expression of CREBL1, IL17BR, KAI1 and Endomucin-2 can be indicative of a healing chronic wound.

In one embodiment the method further involves determine expression levels of any one or more of the following markers: Psoriasin, Claudin-5, IL8RB, IL22R, PTPRK, TEM4, TEM7R, VEGF-C, ARP2 and CAR1. An increased or normal level of expression can be indicative of healing chronic wound.

The methods for identifying healing wounds can include any combination of the molecular markers disclosed in Table 1.

III. Methods of Determining Expression Level

Methods of determining, examining or measuring expression levels can be performed using nucleic acids or protein. In one example, expression levels are determined from an RNA sample. The RNA can be isolated from a sample of wound tissue. The sample of tissue that is examined is assayed for the presence of RNA, preferably total RNA and, more preferably still, the amount of mRNA.

Techniques available for measuring RNA content are well known in the art and routinely practiced by those in the clinical diagnostics field. Such techniques can include reverse transcription of RNA to produce cDNA and an optional amplification step followed by the detection of the cDNA or a product thereof. Examples of detecting nucleic acids include but are not limited to PCR, reverse-transcription PCR, real-time quantitative PCR (Jiang et al 2003a and 2004. Jiang W G, Watkins O, Lane J, Douglas-Jones A, Cunnick G H, Mokbel M, Mansel R E. Prognostic value of Rho family and and rho-GDIs in breast cancer. *Clinical Cancer Research*, 2003a, 9, 6432-6440; Jiang W G, Watkins G, Fodstad O, Douglas-Jones A, Mokbel K, Mansel R E. Differential expression of the CCN family members Cyr61 from CTGF and Nov in human breast cancer. *Endocrine Related Cancers*, 2004, 11: 781-791), northern blot, southern blot, and dot blots.

Alternatively, determining expression levels can involve assaying for the protein encoded by each of the said molecular markers. Protein assays typically, but not exclusively, involve the use of agents that bind to the relevant proteins. Common protein binding agents are antibodies and, most ideally, monoclonal antibodies which, advantageously, have been labelled with a suitable tag whereby the existence of the bound antibody can be determined.

Assay techniques for identifying or detecting proteins are well known to those skilled in the art and are used every day by workers in the field of clinical diagnostics. Such assay techniques can be applied by the skilled worker to utilize the invention. Examples of protein detection assays include, but are not limited to, immunoassays such as enzyme-linked immunosorbent assays (ELISA), western blots, dot blots, radioimmunoassay (RIA), fluoroimmunoassay (FIA), immunoprecipitation and the like.

The level of expression of a given molecular marker can be determined having regard to a reference gene (such as, but not limited to, GAPDH) within a control sample, wherein the control sample is a sample of normal tissue, ideally normal skin tissue, more ideally still, normal tissue taken from the same limb or region as the wound tissue. Thus increased expression refers to an increase in expression of a selected gene having regard to the expression of GAPDH in the respective tissue. Conversely, decreased expression refers to a decrease in expression of a selected gene having regard to GAPDH expression in the respective tissue. Alternatively, the level of expression of a given molecular marker is determined having regard to a reference gene, wherein the reference gene may be the same gene or another selected gene (such as a housekeeping gene) within a control sample, wherein the control sample is a sample of known non-healing, chronic or acute wound tissue, ideally from the same limb or region as the wound tissue to be examined. Alternatively still, the level of expression of a given molecular marker is determined having regard to an internal standard where a genetic construct, such as a plasmid, expressing a known quantity of reference gene is used. Alternatively again, said control is a recognised standard for expression of each relevant gene in a healthy individual.

In all cases the normal, increased or decreased expression was statistically relevant at the 5% level or less.

IV. Methods of Treating Wounds

Methods for treating a wound which involve performing any one or more of the above methods for determining the classification or prognosis of wound tissue in order to identify whether said wound tissue is non-healing chronic wound tissue or healing chronic wound tissue and then selecting an appropriate course of treatment based upon the said classification or prognosis of said tissue are provided.

A. Sample

The sample can be a tissue sample or cell sample. The sample can be taken from normal (control) or wounded areas. The sample can be from a healing or non-healing wound.

The sample can be taken from a mammal. In one embodiment the mammal is human.

B. Kits

Kits for performing any one or more of the aforementioned methods are provided.

The kits can include a probe set for detecting and quantifying the expression level of the following molecular markers: ARP2, CREBL1, VEGF-C, Psoriasin, IL22R, TEM4, IL8RB, IL17BR, Claudin-5, KAI1, PTPRK, CAR1, Endomucin-2, and TEM7R.

In one embodiment the probe set contains those probes useful for detecting and quantifying the expression level of the following molecular markers: ARP2, VEGF-C, Psoriasin, IL22R, TEM4, IL8RB, Claudin-5, PTPRK, CAR1, and TEM7R.

In another embodiment, the probe set includes probes for detecting and quantifying the expression level of the following molecular markers: CREBL1, IL17BR, KAI1, and Endomucin-2.

In another embodiment, the probe set includes probes for detecting and quantifying the expression level of the following molecular markers: ARP2, CREBL1, PTPRK, and TEM7R.

The kits can also include a probe set for detecting and quantifying the expression level of at least one of the molecular markers specified in Table 1 but not shown in Table 3. In one embodiment, all of the molecular markers specified in Table 1 but not shown in Table 3 are detected and quantified.

Microarrays containing any one or more of the aforementioned sets of probes for identifying the expression of any one or more of the aforementioned molecular markers are provided.

Also provided is a kit for determining wound type in a patient wherein the kit includes at least one microarray containing a probe set limited to those for identifying at least one set of the molecular markers described in the above methods. Optionally, a second microarray containing a probe set for identifying the same set of molecular markers in an internal standard that represents the normal level of expression of said markers is provided.

The kits can contain reagents and instructions pertaining to the use of said probes. The instructions can show how to determine expression levels for each of the genes.

The kits can be used for determining the prognosis of mammalian wound tissue.

The probes of the disclosed kits can be used to detect and quantify nucleic acids, such as transcripts, or polypeptides/proteins. The probe sets can contain any combination of probes suitable to detect one or more markers listed in Table 1.

The kits can include any combination of probe sets provided herein or individual probe sets for identifying the aforementioned sets of molecular markers.

In the claims which follow and in the preceding description, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

Reference herein to the term marker is reference to one named gene whose full identity is available on the publically available National Center for Biotechnology Information database or is well known to those skilled in the art (Table 20).

TABLE 20

List of gene transcript tested, name, and accession number

| Name | Accession number |
|---|---|
| Cyr61 | AF307860 |
| CCN2 | NM_001901 |
| CCN3 | NM_002514 |
| Actin | NM_001101 |
| GAPDH | NM_002046 |
| ARP2 | AF006082 |
| TEM4 | AF378754 |
| IL8RB | NM_001557 |
| TEM8 | NM_032208 |
| TEM7R | AF378757 |
| WAVE1 | AF134303 |
| WAVE2 | AB026542 |
| NOTICH1 | AF308602 |
| AMFR | L35233 |
| IL8R | U58828 |
| CMG2 | AY040326 |
| IL17A | NM_002190 |
| PAR4 | AB108448 |
| IL17B | NM_014443 |
| BMP7 | BC004248 |
| CD24 | BC064619 |
| PlGF1 | X54936 |
| Chordinv2 | AF209930 |
| VEGF-D | D89630 |
| IL17BR | AF212365 |
| VEGF-R | E13256 |
| N-WASP | D88460 |
| HGFL | NM_020998 |
| RGMa | NM_020211 |
| VEGF-R2 | AF063658 |
| RGMc | BC085604 |
| IL13 | U70981 |
| BMP15 | NM_005448 |
| Kiss1R | NM_032551 |
| LYN | BC068551 |
| L1CAM | M77640 |
| VEGF | E14233 |
| CD49F | NM_002203 |
| RON | NM_002447 |
| Claudin-5 | NM_003277 |
| BMP9 | AF188285 |
| CD34 | M81104 X60172 |
| CMG1 | AY040325 |
| KAI1 | U20770 |
| OSP-C | NM_001040060 |

TABLE 20-continued

List of gene transcript tested, name, and accession number

| Name | Accession number |
|---|---|
| SATB1 | NM_002971 |
| COM1 | NM_012385 |
| IL17C | NM_013278 |
| TEM1 | XM_006495 |
| IL4 | M13982 |
| OSPA | NM_001040058 |
| WAVE3 | AB026543 |
| TEM6 | AF378756 |
| PEDF | M76979 |
| BMP8 | NM_181809 |
| RHO GDI-G | AF498928 |
| JAK1 | M64174 M35203 |
| AAMP | M95627 |
| SSTR1 | L14865 |
| SATB2 | NM_015265 |
| GDF9A | NM_005260 |
| SHH | L38518 |
| BMP10 | NM_014482 |
| CAR1 | NM_001338 |
| SDF1 | XM_165565 |
| PTPRK | AF533875 |
| ROCK1 | D87931 |
| EHM2 | AB032179 |
| IL24 | BC009681 |
| KISS1 | AY117143 |
| VEGF-C | NM 005429 |
| Chordin V1 | AF209929 |
| STYK1 | NM_018423 |
| Chordin V3 | AF283325 |
| Psoriasin | M86757 |
| β-Catenin | P35222 |
| Endomucin-2 | AB034695 |
| SNAIL | AF131208 |
| RHO-C | L25081 |
| CREBL1 | NM_004381 |
| RHO-8 | AF498969 |
| IL22R | BC029273 |
| FAP | U09278 |
| DRIM | NM_014503 |

All references, including any patent or patent application, cited in this specification are hereby incorporated by reference. No admission is made that any reference constitutes prior art. Further, no admission is made that any of the prior art constitutes part of the common general knowledge in the art.

Preferred features of each embodiment of the invention may be as described in connection with any of the other aspects.

Other features of the present invention will become apparent from the following examples. Thus, features, integers, markers, or genes described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

EXAMPLES

At least 25 molecular markers were tested for their expression levels in chronic and acute wounds (see Table 1).

Tables 5-19 show the data obtained when using the 25 gene molecular signature or the 14 refined gene molecular signature or the 4 gene super refined molecular signature to classify wound tissue.

Methods and Materials

Cells

Cells (A431, HECV, MRC5, HaCaT) were purchased from ATCC, InterLab, ECACC and Gelman Cancer Institute and maintained in tissue culture media supplemented with 10% FCS and antibiotics. Recombinant human HOF was from the applicants' research laboratory. (Metastasis and Angiogenesis Research Group, University Department of Surgery, Cardiff University, Heath Park, Cardiff, CF14 4XN, UK).

Tissue Preparation

Tissues were frozen sectioned on a cryostat (Leica). A portion of the sections were kept for histological analysis. Approximately 20 sections were pooled and homogenised using a hand-held homogenizer using a procedure to extract RNA from the tissues. (See below). RNA extracted from the tissues was quantified and a cDNA bank was generated from equal amount of RNA.

Expression levels of sets of gene transcripts were analysed in a cohort of samples from patients with acute or chronic wounds as well as normal skin. The tissues and normal skins were collected under an approval from the local ethical committee (Ethical approval ID: 05/WSE03192). Written informed consent was obtained from each patient who agreed to a biopsy being taken. Chronic wound tissues were from patients with chronic leg ulcers. Acute wound tissues were obtained from patients with acute surgical wounds after under going excision of pilonidal disease. Normal tissues were from normal volunteers' normal skin.

Extraction of RNA from Cells and Tissues and cDNA Synthesis

Frozen sections of tissues were cut at a thickness of 5-10 μm and were kept for immunohistochemistry and routine histology (Jiang W G, Watkins G, Lane J, Douglas-Jones A, Cunnick G H, Mokbel M, Mansel R E. Prognostic value of Rho family and and rho-GDIs in breast cancer. *Clinical Cancer Research*, 2003a, 9, 6432-6440). A further 15-20 sections were homogenised using a hand-held homogeniser, in ice-cold RNA extraction solution (RNA isolation reagent, ABgene, Surrey, England). The concentration of RNA was determined using a UV spectrophotometer (Jiang W G, Watkins G, Lane J, Douglas-Jones A, Cunnick G H, Mokbel M, Mansel R E. Prognostic value of Rho family and rho-GDIs in breast cancer. *Clinical Cancer Research*, 2003a, 9, 6432-6440). Reverse transcription was carried out using a RT kit with an anchored oligo-dt primer supplied by AbGene Ltd, Surrey, England, UK, using 1 μg total RNA in a 96-well plate. The quality of cDNA was verified using β-actin primers. The RNA extraction kit and RT kit were obtained from AbGene. PCR primers (see Table 2) were designed using Beacon Designer (California, USA) and synthesized by Invitrogen™ Ltd (Paisley, Scotland, UK). Molecular biology grade agarose and DNA ladder were from Invitrogen. Mastermix for routine PCR and quantitative PCR was from AbGene.

Quantitative Analysis of Genetic Markers

The transcript level of the said genes (Tables 1 and 3) from the above-prepared cDNA was determined using a real-time quantitative PCR, based on the AMPLIFLUOR Universal Detection System technology (Nazarenko I A, Bhatnagar S K, Hohman R J. A closed tube format for amplification and detection of DNA based on energy transfer. Nucleic Acids Res. 1997 Jun. 15; 25(12):2516-21); modified from a method previously reported (Jiang W G, Watkins G, Lane J, Douglas-Jones A, Cunnick G H, Mokbel M, Mansel R E. Prognostic value of Rho familty and and rho-GDIs in breast cancer. *Clinical Cancer Research*, 2003a, 9, 6432-6440; and Jiang W G, Douglas-Jones A, and Mansel R E. Level of expression of PPAR-gamma and its co-activator (PPAR-GCA) in human breast cancer. *International Journal of Cancer,* 2003b, 106, 752-757). Briefly, a pair of PCR primers (see Table 2) were designed using the Beacon Designer software (version 2, Biosoft, Palo Alto, Calif., USA). To one of the primers (routinely to the antisense primer in our laboratory), an additional sequence, known as the Z sequence (5' actgaacctgaccgtaca'3; nucleic acids 1-18 of SEQ ID NOs:2, 4, 6, 8, 10, 12, 14, 16, 18, 20, 22, 24, 26, 28, 30, 32, 34, 36, 38, 40, 42, 44, 48, and 50) which is complementary to the universal Z probe (Nazarenko et at 1997, as above) (Intergen Inc., England, UK), was added. A Taqman™ TAQMAN detection kit for β-actin was purchased from Perkin-Elmer, Buckinghamshire, United Kingdom.

The reaction was carried out using the following: Hot-start Q-master mix (Abgene), 10 pmol of specific forward primer, 1 pmol reverse primer which has the Z sequence, 10 pmol of FAM (carboxyfluorescein)-tagged probe (Intergen Inc.), and cDNA from approximate 50 ng RNA (calculated from the starting RNA in the RT reaction). The reaction was carried out using the IcyclerIQ™ Real Time PCR Detection System (Bio-Rad™, Hemel Hamstead, England, UK) which is equipped with an optic unit that allows real time detection of 96 reactions, using the following condition: 94° C. for 12 minutes, 50 cycles of 94° C. for 15 seconds, 55° C. for 40 seconds and 72° C. for 20 seconds (Jiang W G, Douglas-Jones A, and Mansel R E. Level of expression of PPAR-gamma and its co-activator (PPAR-GCA) in human breast cancer. *International Journal of Cancer,* 2003b, 106, 752-757 and Jiang W G, Grimshaw D, Lane J, Martin T A, Parr C, Davies G, Laterra J, and Mansel R E. Retroviral hammerhead transgenes to cMET and HGF/SF inhibited growth of breast tumour, induced by fibroblasts. *Clinical Cancer Research,* 2003c, 9, 4274-4281). The levels of the transcripts were generated from an internal standard (Jiang W G, Watkins G, Lane J, Douglas-Jones A, Cunnick G H, Mokbel M, Mansel R E. Prognostic value of Rho family and rho-GDIs in breast cancer. *Clinical Cancer Research,* 2003a, 9, 6432-6440) that was simultaneously amplified with the samples. The results are shown here in two ways: levels of transcripts based on equal amounts of RNA, or as a target/GAPDH ratio.

Deciphering the Expression Pattern and Deduction of the Molecular Signature

The pattern of expression of the gene transcripts was first analysed against the nature of the samples using Minitab software (Minitab Inc., State College, Pa. 16801, USA). 'refining' means the selection of potential candidates. This selection is based on a Macro (WD-Sig Macro) written for the study cohort that allows automatic statistical analysis of expression levels in different tissue types within the Minitab application window. 'selection of final list' is based on the characteristics of a given gene transcript and its ability to discreetly separate the chronic group from other groups. This involved the use of Excel (Microsoft Office 2007 version, used for grouping and calculation of basic statistics), SPSS (SPSS Inc., Chicago, Ill., US, for advanced statistical analysis within the three groupings) and Minitab analysis (for nonparametric Kriskul Wallis test) tool. 'compilation of expression signature' is based on an 'add one and minus one' procedure by using the multiple cells tabulation methods, using a macro written for the study. The macro allows one to automatically and rapidly conduct statistical analysis within Minitab software, after removing candidate genes from the list. However, as those skilled in the art will appreciate, other forms of analysis may be used to assess the data and so determine which genes contribute most to the predicative nature of the assay. These alternative forms of analysis include logistic regression using either a weighted or nonweighted analysis. In the weighted analysis those genes present in the signature or 'model' which more closely predict healing added more to the prognostic score than a gene with less of a relationship to healing. Also, if the presence of a gene is associated with 'non-healing' rather than 'healing' it will have a negative impact on the score. Additionally, backward or stepwise elimination analysis may be used. In the former instance, genes are eliminated from the predictive signature having regard to their contribution towards the predictive power of the signature or 'model' until only genes with a pre-selected statistical significance remain. In the latter instance, genes are included or eliminated from the predictive signature based upon a statistical criteria of acceptance. Additionally, and optionally, shrinkage methods can be used to adjust the weighting of each gene in a given data set, this latter procedure is preferred when the data sets are small e.g. including less than 10 events such as less than 10 healed wounds.

Manufacturing the 'Refined' Kit.

After finalising the gene signature, the testing kit was manufactured based on the signature, by first making up all the test materials for the test genes and then automatically pipetting into 96 well plates, which were ready for use in testing clinical and cell materials. The kit was made in the laboratory and stored at −20° C. until use.

In Vitro Wound Assays and Validation Studies

Monitoring the Healing Process Using Electric Cell Sensing (ECIS)

The ECIS 1600R model instrument and 8W10 arrays (Applied Biophysics Inc, N.J., US) were used in the study. After treating the array surface with a Cysteine solution, the arrays were incubated with complete medium for 1 hour. The same number of lung cancer cells, HaCat, A431 and HECV (200, 000 per well) were added to each well (cell free was the control). The cells were then immediately subjected to wounding using the integrated elevated field module in the instrument in the 1600R model (5v, 30 seconds for each well). The changes of cellular impedance were immediately recorded after wounding (400, 4000 and 40,000 Hz). The data was analysed using the ECIS RbA modelling software, supplied by the manufacturer. At the respective time point, images from cells were taken to verify the healing status of the cells.

Monitoring the Healing Process Using Time-Lapsed Videography

In order to ascertain the healing process as seen in ECIS and in a scratch wounding assay, the healing was monitored morphologically using the following two methods on a time lapse video: electric induced wounding and scratch wounding assays. The former was based on the ECIS model, in which a confluent monolayer of cells was electronically wounded and the healing (migration of cells into the wounding space over the electrode) was monitored (before and after wounding). The latter was based on scratching the monolayer of cells using a fine plastic scraper, followed by monitoring. The monitoring lasted for up to 6 hours or until the wound closed.

Validation Studies Using In Vitro Cell Models

Human endothelial cells, fibroblasts, melanoma cells, and keratinocytes were used. Cells or cell mixtures were allowed to reach confluence in a 6 well plate. They were then wounded using a plastic scraper. Multiple wounds (20) were created in each well. A wounded cell layer was allow to recover over 1 hour, 2 hours, 4 hours and 7 hours periods, representing the 'acute' (1 and 2 hours) and 'healed' (4 and 7 hours) phases of the study (deduced from, FIG. 1). RNA was extracted and cDNAs were generated as above. The expression profile of the wound signature was tested on these samples.

Statistical Analysis

Statistical analysis was conducted using Minitab, SPSS and an online Chi-square service tool.

Results

Identification of Wound Signatures 34 human tissues were used, which comprised 14 chronic wound tissues, 10 acute wound tissues and 10 normal skins.

3 sets of gene signatures were obtained:

WDsig-1: this has a list of 25 genes that allow evaluation of the fate of a given wound and guidance for treatment (gene list in Table 1).

WDsig-2: this refined molecular signature was deduced from WDsig-1 and has a list of 14 genes which form the final list of a first product and allows one to predict the fate of a wound (gene list in Table 3)

WDsig-3: this super refined molecular signature was deduced from WDsig-2 and has a list of 4 genes which form the final list of a second product and allows one to predict the fate of a wound (gene list in Table 4)

Wound Signatures and Healing of Wounds

The refined molecular signatures WDsig-2 allows clear distinction of a chronic wound from acute wound and normal skin.

Two criteria have been used to distinguish the wounds:

(1) To predict the nature of the wound by distinguishing chronic wounds from acute wounds and normal skin with near 'zero' overlapping a calculation pattern (referred to here as AO10) was obtained that returns with a Chi-square value of 25.33 (p=0.00000316). 100% of chronic wounds were predicted and 90% of acute wounds predicted. (Table 5); and

TABLE 5

Prediction of wound healing using AO > 10

|   | 0 | 1 |
|---|---|---|
| 1 | 14 | 0 |
| 2 | 9 | 1 |
| 3 | 1 | 9 |

$X^2 = 25.33$, p = 0.00000316, Yate's p = 0.00003741
(note:
in vertical columns: 1 = chronic wound; 2—normal skin, 3 = acute wound; in horizontal rows: 0, 1 are signature Ids)

(2) To predict the nature of the wound by distinguishing chronic wounds from acute wounds with 'zero' overlapping a calculation pattern (referred to here as AO123d) was obtained that returns with a Chi-square value of 25.868 (p=0.00000268). 100% of chronic wounds were predicted and 100% of acute wounds predicted. (Table 6).

TABLE 6

Prediction of the healing wound using the AO123d three set format.

|   | 1 | 2 | 3 |
|---|---|---|---|
| 1 | 14 | 0 | 0 |
| 2 | 9 | 1 | 1 |
| 3 | 1 | 9 | 9 |

$X^2 = 25.868$, p = 0.00003364, Yate's p = 0.00054889
(note:
in vertical columns: 1 = chronic wound; 2—normal skin, 3 = acute wound) In Horizontal rows: 1, 2, 3 are signature IDs)

In Table 7 acute wounds are shown to be clearly distinguished from chronic wounds, using the F5>5 format of data analysis. The refined signature provided a clear distinction between the two types of wounds (p=0.00000676).

TABLE 7

Distinguishing the chronic from acute using the refined F5 > 5 format

|   | 0 | 1 |
|---|---|---|
| 1 | 14 | 0 |
| 3 | 1 | 9 |

$X^2 = 20.26$, p = 0.00000676, Yate's p = 0.00004297
(note:
in Horizontal rows: 1 = chronic wound; 2 = normal skin, 3 = acute wound)
In vertical columns: 0, 1 are signature IDs)

Tables 8 and 9 show how to distinguish acute wounds from normal skin (Table 8) and chronic wounds from normal skin (Table 9). As shown in the respective tables, the refined molecular signature also provides distinction between normal skin and acute or chronic wounds, respectively, although the statistical power is weaker for normal/chronic wounds.

TABLE 8

Distinguishing the acute from normal skin in two set format (8a-1left, F5-5) or three set format (right ao123) using the refined signature Table 8a

|   | 0 | 1 |
|---|---|---|
| 2 | 8 | 2 |
| 3 | 0 | 10 |

$X^2 = 13.333$, p = 0.00026078, Yate's p = 0.00139833

Table 8b

|   | 1 | 2 | 3 |
|---|---|---|---|
| 2 | 6 | 4 | 0 |
| 3 | 0 | 2 | 8 |

$X^2 = 14.667$, p = 0.00065328, Yate's p = 0.0053589
(note:
in Horizontal rows: 1 = chronic wound; 2 = normal skin, 3 = acute wound)
In vertical columns: 0, 1 are signature IDs)

TABLE 9

Distinguishing the chronic from normal skin in two set format (9b1, F2-8) or three set format (6b2 bd123) using the refined signature Table 9a

|   | 0 | 1 |
|---|---|---|
| 1 | 14 | 0 |
| 2 | 7 | 3 |

$X^2 = 4.8$, p = 0.02846, Yate's p = 0.1176

Table 9b

|   | 1 | 2 | 3 |
|---|---|---|---|
| 1 | 13 | 0 | 1 |
| 2 | 7 | 3 | 0 |

$X^2 = 5.280$, p = 0.07136, Yate's p = 0.3144
(note:
in vertical columns: 1 = chronic wound; 2—normal skin, 3 = acute wound)
In Horizontal rows: 0, 1, 2, 3 are signature IDs)

Moreover, work using the WDsig-1 also allows a clear distinction between chronic wound, acute wound and normal skin.

Two criteria to distinguish the wounds have been used:
(1) To distinguish acute wound from chronic wounds and normal skin, a two group fashion was used (see Table 10).

TABLE 10

Prediction of the healing wound using
the full list of the signature All19

|   | 0 | 1 |
|---|---|---|
| 1 | 13 | 1 |
| 2 | 7 | 3 |
| 3 | 1 | 9 |

$X^2 = 17.365$, p = 0.00016953, Yate's p = 0.00101031
(note:
in Horizontal rows: 1 = chronic wound; 2—normal skin, 3 = acute wound)
In vertical columns: 0, 1 are signature IDs)

(2) To distinguish chronic wounds from acute wounds and normal skin, a three group fashion was used (see Table 11).

TABLE 11

Prediction of the healing wound using
the full list of the signature All19abc

|   | 1 | 2 | 3 |
|---|---|---|---|
| 1 | 13 | 0 | 1 |
| 2 | 7 | 1 | 2 |
| 3 | 1 | 0 | 9 |

$X^2 = 21.325$, p = 0.00027298, Yate's p = 0.00415619
(note:
in vertical columns: 1 = chronic wound; 2—normal skin, 3 = acute wound)
In Horizontal rows: 1, 2, 3 are signature IDs)

Validation of Signatures Using In Vitro Wound Healing Model.

The validation was first carried out using the ECIS model and wounding assay in order to obtain the best time point(s) for such a study, following which, the analysis was carried out using the manufactured refined molecular signature kit.

In Vitro Wounding Model and Point of Monitoring.

Figure 2:
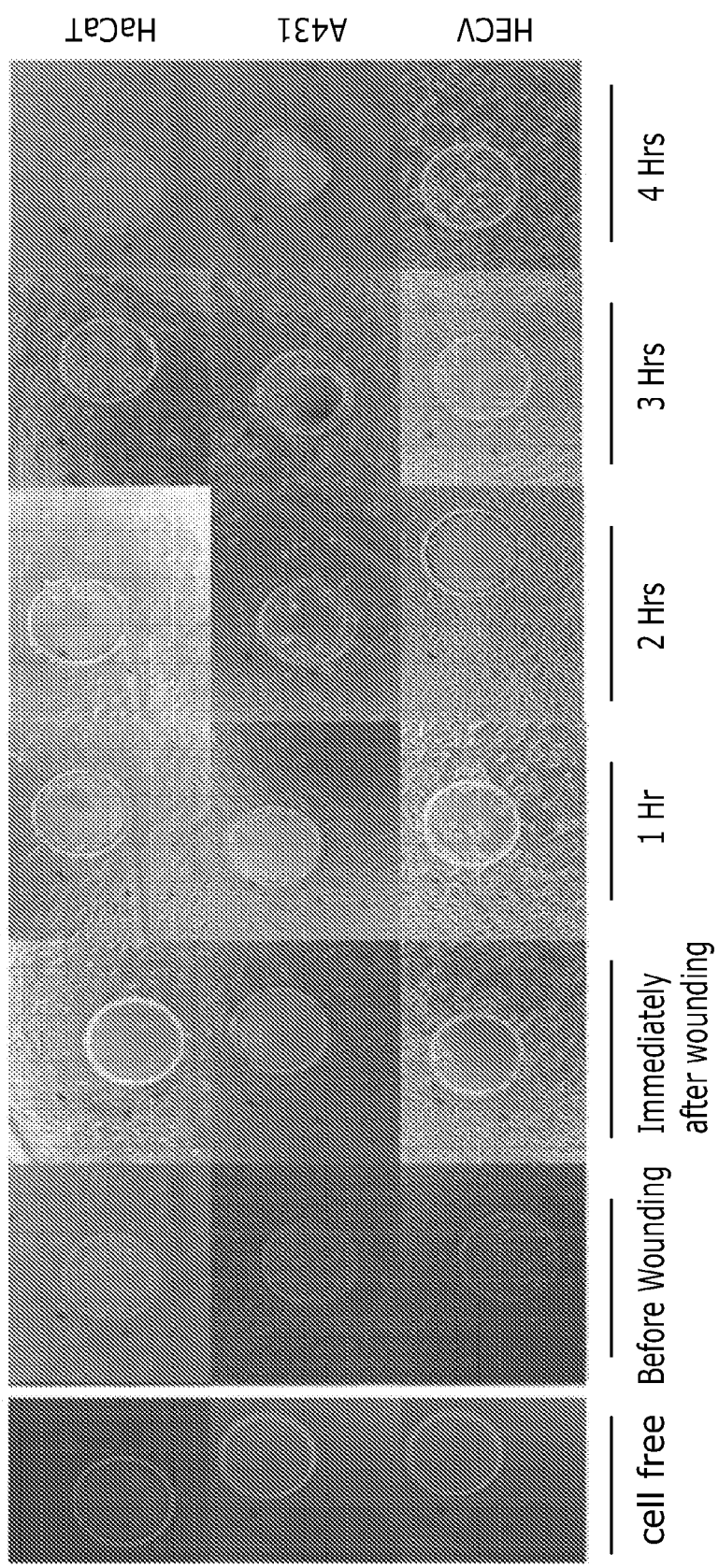
FIG. 2 shows morphological evaluation of wounding using the ECIS based wounding assay. Confluent cells on electrode were wounded at 6 v for 60 seconds, after which the migration of cells into the wounding space was recorded over a 4 hour period. After 3 hours, the wounds were largely healed.
Figure 3:
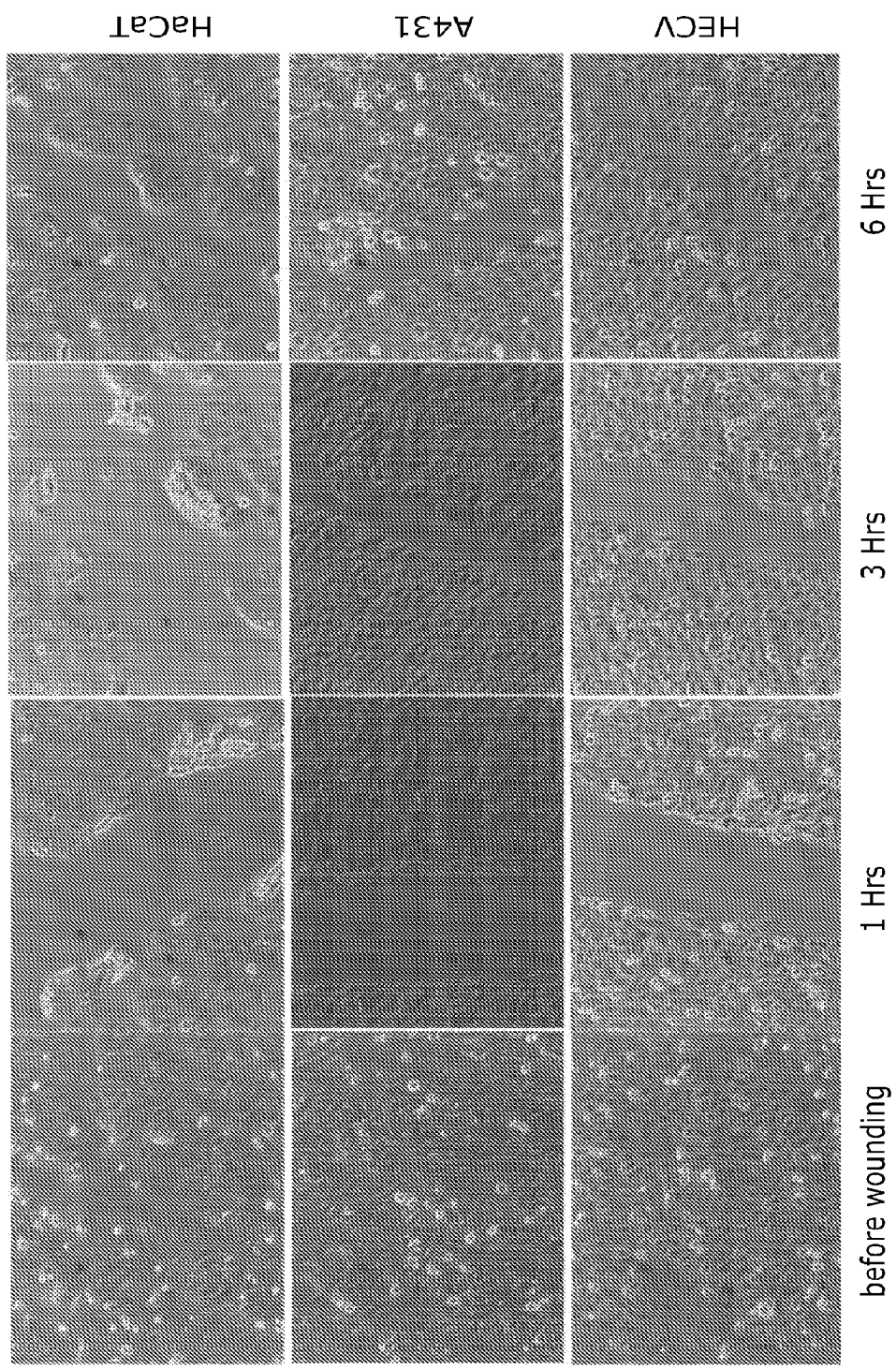
FIG. 3 shows morphological evaluation of wounding using the scratch wounding assay. Confluent cells on electrode were wounded, after which the migration of cells into the wounding space was recorded over a 6 hour period. After 3 hours, the wounds were largely healed.

This experiment was to determine the appropriate time points for the 'acute' and 'chronic/healed' phases. Cell monolayer was electrically wounded and the healing process recorded. As shown in FIG. 1, 1-2.5 hours after wounding, the healing process was in its linear phase, thus representing the best time point for a rapid (acute) healing process. After 3 hours, the healing process reached its stable phase, thus representing the 'healed/stable' stage. The unwounded cells; 2 hours; and 4 hours were therefore chosen to represent the three possible stage of healing: unwounded, acute and healed. The electric signal was fully supported by the morphological changes of the cells (FIGS. 2 and 3).

A431 Cell Model.

The A431 cell model has been used for wounding and monitoring time points. The initial validation was based on a cell model, which may reflect the healing nature of a human wound: the co-cultured endothelial, fibroblasts and epithelial cells. Here, HECV endothelial cells, MRC5 fibroblasts and A431 melanocytes, in a ratio of 20:10:100, were allowed to reach confluence. The cells were wounded. The recovery allowed for 1 hour, 2 hours and 4 hours. The non-wounded monolayer was used as non-wound, 2 hours after wounding was acute wounding where the repair is at the most active stage, and 4 hours after wounding was near complete healing (as the wounds were mostly closed).

The refined molecular signature showed the rapid rise of expression profile during the 'acute' phase. The signature of expression returns to normal 'non-wounded' level. As shown in the following table, the pattern of expression and the power of prediction of the 'in vitro wounding healing' is similar to that seen in human wounds (p=0.00000374, Table 12).

TABLE 12

Validation study using the refined signature kit
on in vitro wound healing: the A431/H/M model.

|   | low | Unchange | rise |
|---|---|---|---|
| Healed | 6 | 5 | 0 |
| Unwounded | 0 | 11 | 0 |
| 'acute' | 2 | 1 | 8 |

$X^2 = 31.941$ WITH D.F. = 4, p = 0.00000374

HaCat Cell Model.

Similar to the A431 model, a similar pattern was seen with the HaCaT cell model. The keratinocytes migrate at a slower pace. The healing stage was therefore divided into acute (3 hours) and healed (6 hours). The change of gene pattern resulted in a significant difference between the unwounded, acute and healed (p=0.003887, Table 13).

TABLE 13

Validation study using the refined signature kit
on in vitro wound healing: the HaCaT model.

|   | low | rise |
|---|---|---|
| Healed | 7 | 3 |
| Unwounded | 10 | 0 |
| 'acute' | 3 | 7 |

$X^2 = 11.1$ WITH D.F. = 2, p = 0.003887

Endothelial Cell Model.

Using the endothelial cell wounding model, the change of the refined signature was also found to be highly significant (Table 14).

TABLE 14

Validation study using the refined signature kit on in vitro
wound healing: the HECV endothelial model (set-2).

|   | low | rise |
|---|---|---|
| Healed | 8 | 4 |
| Unwounded | 12 | 0 |
| 'acute' | 1 | 11 |

$X^2 = 21.257$ WITH D.F. = 2, p = 0.00002422

The Endothelial/fibroblast co-culture model was further adopted by plate HECV and MRC5 cells at a ratio of 5:1. A wounding assay using this cell model showed a similar change of gene expression pattern (Table 15).

TABLE 15

Validation study using the refined signature kit on in
vitro wound healing: the HECV-fibroblast model (set-2).

|   | low | rise |
|---|---|---|
| Healed | 7 | 3 |
| Unwounded | 10 | 0 |
| 'acute' | 9 | 1 |

$X^2 = 17.5$ WITH D.F. = 2, p = 0.0001584

Validation Study Using the Gene Signature.

In order to verify the validity of the gene signature and if the signature was able to distinguish chronic healed wounds and chronic non-healing wounds, we tested our 14-gene signature on an independent cohort, which was comprised of 51 chronic non-healing wounds and 20 chronic healed wounds.

The fresh frozen wounds tissues were all of venous ulcer of aetiology. They were biopsied at the time of visit to the clinic (time zero), after which patients were treated and followed up routinely in the clinic. Wounds which were healed within 3 months after the initial visit were classified as 'Chronic healed', and those not healed within the time frame were classified as 'Chronic non-healing'. Patients with signs of clinical infection were also recorded. The samples were blinded before processing and only decoded after the final test.

Genetic materials were similarly extracted as aforementioned. The test on this independent cohort was based on the 14 gene signature using real time quantitative RT-PCR as aforementioned.

The 14-Gene Signature Significantly Distinguished Chronic Healed from Chronic Non-Healing Wounds Using a similar two-way division to the one shown in Table 8, a non-healing signature was seen in 98% (50/51) of the patients with non-healing wounds, and in 40% (8/20) of the chronic healing wounds (Table 16).

TABLE 16

The 14-gene signature clearly distinguished chronic healed and non-healing wounds.

| Chronic tissues | 0 | 1 | Total |
|---|---|---|---|
| Non-healed | 50 | 1 | 51 |
| healed | 8 | 12 | 20 |

$X^2 = 32.254$, $P = 0.00000001$ (Yate's $X^2 = 28.59$, $P = 0.00000009$)
(note:
in vertical columns: nature of heaing, in Horizontal rows: 0, 1 are signature IDs)

Using a similar three-way division to the one shown in Table 9, a similar significant differentiation between the chronic healed and chronic non-healing wounds was seen. In this way, 47% (24/51) of the patients with chronic non-healing wounds had the non-healing signature, and no patients with chronic healed wounds had the non-healing signature (table 17).

TABLE 17

The three way classification of wounds by the 14-gene signature clearly distinguished chronic healed and non-healing wounds.

| Chronic tissues | 1 | 2 | 3 | Total |
|---|---|---|---|---|
| Non-healed | 24 | 25 | 2 | 51 |
| healed | 0 | 8 | 12 | 20 |

$X^2 = 35.78$, $P = 0.00000002$ (Yate's $X^2 = 31.227$, $P = 0.00000017$)
(note:
in vertical columns: nature of heaing, in Horizontal rows: 1 = non-healing signature, 3 = healing signature, 2 = signature 'uncertain'.

Distinguishing the Healed and Non-Healing Chronic Wounds by the 14-Gene Signature is Independent of the Presence of Infection In the 51 patients with chronic non-healing wounds, 7 had clinical signs of infections. The samples were further analyzed to see if the difference between tissues with different gene signature is dependent on the presence of infection. Only 1 of the 44 patients with no signs of infection had a healing signature, the remaining 43 out of 44 had a non-healing signature. All those patients with infection had the non-healing signature (7/7). This indicates that the prediction of healing and non-healing is independent upon infection (Table 18).

TABLE 18

The differentiation of non-healing wounds by the 14-gene signature is independent of infection.

| Chronic non-healing | 0 | 1 | Total |
|---|---|---|---|
| No Infection | 43 | 1 | 44 |
| Signs of infection | 7 | 0 | 7 |

$X^2 = 0.162$, $P = 0.687$ (Yate's $X^2 = 1.133$, $P = 0.287$)
(Note:
0 = non-healing signature, 1 = healing signature).

Statistical Analysis:

This was as previously described. Patients were divided into either 'two-way grouping' or 'three-way grouping', based on the genetic signature. Statistical test was Chi-square test.

The 4-Gene Signature Significantly Distinguished Chronic Healed from Chronic Non-Healing Wounds Using a similar two-way division to the one shown in Table 8, a non-healing signature was seen in 90% (46/5) of the patients with non-healing wounds, and in 35% (7/20) of the chronic healing wounds (Table 19).

TABLE 19

The 4 gene, PTPRK, Creb1, ARP2 and TEM7R signature:

| Chronic tissues | 0 | 1 | Total |
|---|---|---|---|
| Non-healed | 46 | 5 | 51 |
| healed | 7 | 13 | 20 |

$X^2 = 20.03$, $P < 0.001$ (Fisher's $P < 0.001$)
Fisher exact test (more appropriate in this case): $p < 0.001$
Chi square test: Chi-square value = 20.03, $p < 0.001$ Discussion The present data have provided two novel tools to distinguish between non-healing chronic or healing chronic wounds. It is believed that the molecular signatures described herein are the first such signatures derived from a clinical setting. In addition, the validation study using in vitro cell models has shown the validity of the signatures in evaluating the healing process.

The biological impact of the signatures can be read from the nature of the candidates genes in each signature. The signature list comprises clusters that link to cell migration (ARP2, KAI1, CAR-1), angiogenesis/lymphangiogenesis (VEGF-C, TEM-4, TEM7R), gene transcription regulation (CREBL1), immune functions (IL-8RB, IL-22R, IL17BR), regulation of cellular adhesion behaviours (PTPRK, Claudin-5) and genes that link to skin disorder (Psoriasin). The diversity and complexity of the list therefore reflects the complex biological process underlying the healing process of a wound.

The validation study on an independent cohort further revealed the pivotal application of the genetic prognostic tests in predicting the nature of wound healing. Using this cohort of chronic wound tissues with a single aetiology (venous ulcer) and in a double blinded test, the test clearly differentiated those wounds that healed from those that were non-healing (within 3 months). Collectively, it is concluded that the gene signatures reported here provide vital information in predicting the clinical outcome of the nature of healing (to heal or to become chronic) and the long term outcome of the healing (chronic but healed within 3 months or chronic but unable to healed within 3 months (non-healing)).

Thus, the clinical application is evident. A test using the signature on a given wound tissue would allow one immediately to distinguish the fate of the wound.

In this study, in vitro wound assays were adopted in order to evaluate if the changes in molecular signature seen in human wounds may be mirrored in vitro. We used two models to create cell wounds; to obtain the dynamics of the healing process. Using the ECIS model, both the ECIS trace and morphological observations have indicated that under the specified conditions, wound healing is at its linear phase between 0.5-3 hours after wounding. 4 hours after wounding, the wounds are virtually closed 'healed'. This is of course dependent upon the type of cells, i.e. endothelial cells and melanoma cells healed at a faster pace than keratinocytes. This is fully supported by the conventional scratch wounding assay (FIGS. 1 and 2). Using this cell model, it was shown that the signature seen in human wounds is mirrored in vitro.

In summary, the current study describes new molecular signatures that allow the classification and prognosis of the nature of human wounds: if a wound is to eventually heal or to become a non-healing chronic wound.

We claim:

1. A method for identifying abnormal or non-healing chronic mammalian would tissue, which method comprises:
   a) amplifying, by PCR, a combination of molecular markers Psoriasin, Claudin-5, IL8RB, IL22R, PTPRK, TEM4, TEM7R, VEGF-C, ARP2, and CARI from said sample of wound tissue;
   b) determining the level of expression of said combination of said molecular markers; and
   c) concluding, when an increased level of expression of each of the molecular markers compared to a control is seen, that the wound is an abnormal or non-healing chronic wound;
   wherein said step of amplification step (a) is performed with the primer sets:

Psoriasin:  SEQ ID NO: 37, SEQ ID NO: 38;
   Claudin-5:  SEQ ID 21, SEQ ID NO: 22;
   IL8RB:      SEQ ID NO: 19, SEQ ID NO: 20;
   IL22R:      SEQ ID NO: 15, SEQ ID NO: 16;
   PTPRK:      SEQ ID NO: 25, SEQ ID NO: 26;
   TEM4:       SEQ ID NO: 41, SEQ ID NO: 42;
   TEM7R:      SEQ ID NO: 23, SEQ ID NO: 24;
   VEGF-C:     SEQ ID NO: 7, SEQ ID NO: 8;
   ARP2:       SEQ ID NO: 1, SEQ ID NO: 2;
   CAR1:       SEQ ID NO: 47, SEQ ID NO: 48;
   Endomucin:  SEQ ID NO: 13, SEQ ID NO: 14;
   IL7BR:      SEQ ID NO: 43, SEQ ID NO: 44;
   Kal1:       SEQ ID NO: 45, SEQ ID NO: 46; and
   CREBL1:     SEQ ID NO: 49, SEQ ID NO: 50.

2. The method of claim 1 further including:
   determining the levels of expression of the combination of molecular markers Endomucin-2, IL17BR, Kal1 and CREB L1; and
   concluding, when a decreased or normal level of expression of the molecular markers Endomucin-2, IL17BR, Kal1 and CREB L1 is seen compared to a control, that the wound is a non-healing chronic wound;
   wherein said step of determining the level of expression of the molecular markers is determined by PCR using the molecular marker primer sets:
   Endomucin-2: SEQ ID NO: 13, SEQ ED NO: 14;
   IL7BR: SEQ ID NO: 43, SEQ ID NO 44;
   Kal1: SEQ ID NO: 45, SEQ ID NO: 46; and
   CREBL1: SEQ ID NO: 49, SEQ ID NO: 50.

3. The method of claim 1 wherein the tissue is human tissue.

4. The method of claim 1 wherein the said levels of expression of molecular markers are determined by comparison to a level of expression of a reference molecular marker and so increased or decreased expression refers to increased or decreased expression with reference to the expression of said reference molecular marker.

5. The method of claim 4 wherein said reference molecular marker is a gene expressed within a control sample of tissue.

6. The method of claim 5 wherein said control sample is normal skin tissue.

7. The method of claim 6 wherein said normal skin tissue is taken from the same limb or region as said sample of wound tissue.

8. The method of claim 4 wherein said reference molecular marker is a housekeeping gene.

9. The method of claim 8 wherein said reference gene is GAPDH.

\* \* \* \* \*